(12) United States Patent
Gibson et al.

(10) Patent No.: US 9,278,010 B2
(45) Date of Patent: Mar. 8, 2016

(54) PATIENT-MATCHED ACETABULAR ALIGNMENT TOOL

(75) Inventors: Luke Andrew Gibson, Southaven, MS (US); Lauren Christina Jasper, Memphis, TN (US); Phillip E. Frederick, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 291 days.

(21) Appl. No.: 13/816,132

(22) PCT Filed: Aug. 16, 2011
(Under 37 CFR 1.47)

(86) PCT No.: PCT/US2011/047905
§ 371 (c)(1),
(2), (4) Date: Sep. 19, 2013

(87) PCT Pub. No.: WO2012/024288
PCT Pub. Date: Feb. 23, 2012

(65) Prior Publication Data
US 2014/0052137 A1    Feb. 20, 2014

Related U.S. Application Data

(60) Provisional application No. 61/373,993, filed on Aug. 16, 2010.

(51) Int. Cl.
*A61F 2/46* (2006.01)
*A61B 17/17* (2006.01)
(Continued)

(52) U.S. Cl.
CPC ........... *A61F 2/4609* (2013.01); *A61B 17/1746* (2013.01); *A61B 2017/568* (2013.01);
(Continued)

(58) Field of Classification Search
CPC .................................................. A61B 17/1746
See application file for complete search history.

(56) References Cited

U.S. PATENT DOCUMENTS 2,282,285 A    5/1942    Olson
6,395,005 B1   5/2002    Lovell
(Continued)

FOREIGN PATENT DOCUMENTS

CN    101711695 A    5/2010

OTHER PUBLICATIONS

Chinese Patent Office, China First Office Action, dated Nov. 3, 2014, 11 pages with English translation.
(Continued)

*Primary Examiner* — Andrew Yang
(74) *Attorney, Agent, or Firm* — Taft Stettinius & Hollister LLP

(57) ABSTRACT

Systems, devices, and methods are provided for aligning acetabular implants. A patient-matched acetabular alignment tool is used to orient tools and implants intraoperatively. The patient-matched acetabular alignment tool includes a mounting member and leg members which are configured based on the particular patient's anatomic landmark sites (e.g., acetabular bony landmarks). The leg members are attached to the mounting member and configured to connect with a respective anatomic landmark site to achieve a desired implant angle and axis. For example, the leg members may form a tripod support base through which an acetabular shell may be inserted into the patient's acetabulum at desired angles of version and inclination. In some embodiments, the leg members may be retractable and expandable with respect to the mounting member, thereby providing a tool with reduced profile for inserting the device in the patient's soft tissue.

45 Claims, 10 Drawing Sheets

(51) Int. Cl.
    *A61B 17/56* (2006.01)
    *A61F 2/30* (2006.01)

(52) U.S. Cl.
    CPC ..... *A61F2/30942* (2013.01); *A61F 2002/4628* (2013.01); *A61F 2002/4629* (2013.01); *A61F 2002/4687* (2013.01)

(56) References Cited

U.S. PATENT DOCUMENTS 6,935,005 B2    8/2005  Avery
2010/0082035 A1*  4/2010  Keefer .......................... 606/91

OTHER PUBLICATIONS

European Office Action; European Patent Office; European Patent Application No. 11818658.4; Oct. 2, 2015; 4 pages.
Mexican First Office Action; Mexican Patent Office; Mexican Patent Application No. MX/A/2013/001951; Apr. 17, 2015; 8 pages.
Russian Office Action; Russian Patent Office; Russian Patent Application No. 2013110369; Jul. 2, 2015; 6 pages.
Chinese Search Report; Chinese Patent Office; Chinese Application No. 201180049963.5; Aug. 12, 2015; 5 pages.
Chinese Second Office Action; Chinese Patent Office; Chinese Application No. 201180049963.5; Aug. 21, 2015; 28 pages.

* cited by examiner

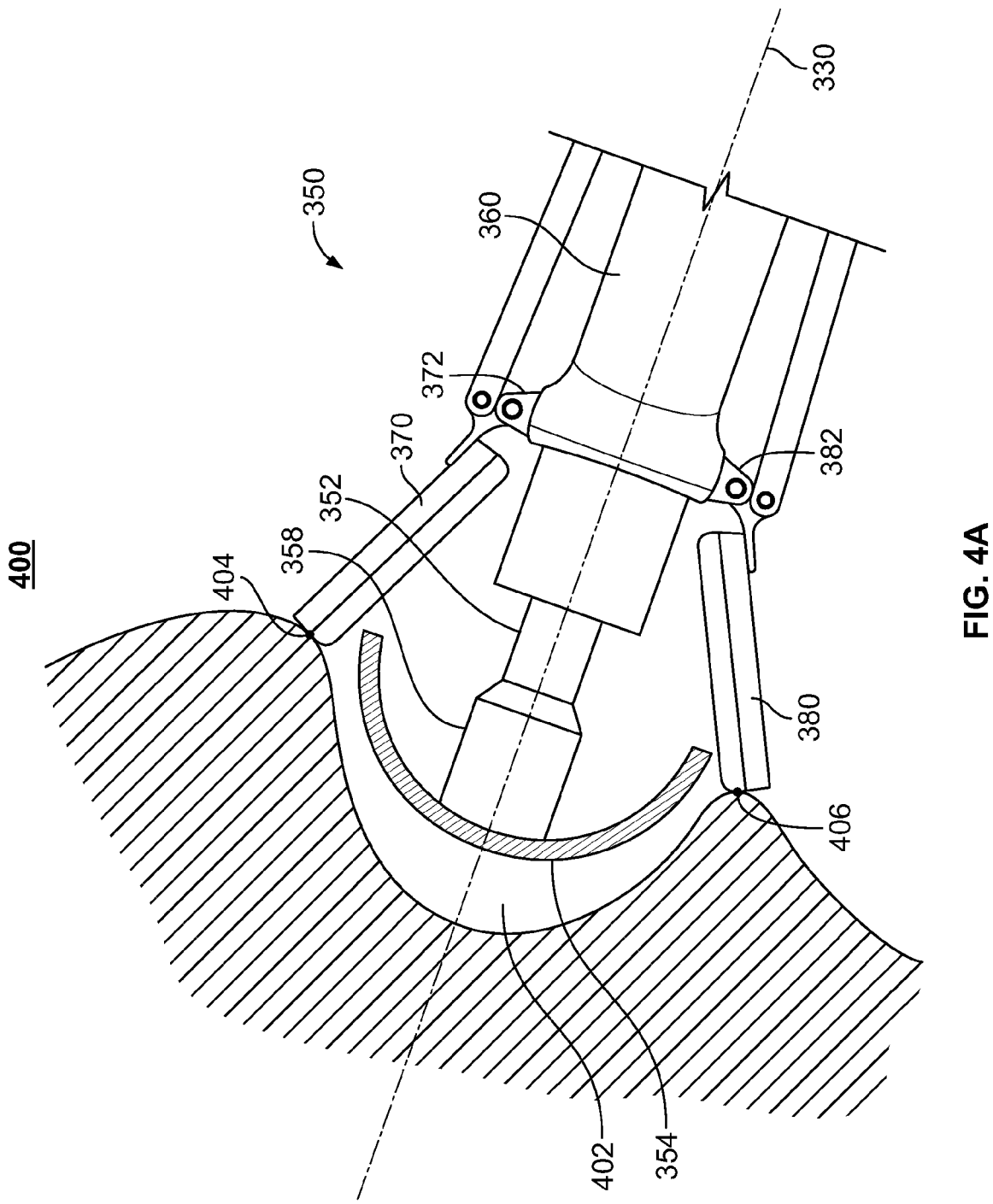

PATIENT-MATCHED ACETABULAR ALIGNMENT TOOL

CROSS-REFERENCE TO RELATED APPLICATIONS

This application is a U.S. National Phase filing of International Application No. PCT/US11/047905 filed on Aug. 16, 2011 which claims the benefit of U.S. Provisional Patent Application No. 61/373,993, filed Aug. 16, 2010, both of which are hereby incorporated by reference herein in their entirety.

BACKGROUND

Joints often undergo degenerative changes due to a variety of reasons. When joint degeneration becomes advanced or irreversible, it may become necessary to replace the natural joint with a prosthetic joint. Artificial implants, including hip joints, shoulder joints, and knee joints are widely used in orthopedic surgery. Specifically, hip joint prostheses are common. The human hip joint acts mechanically as a ball and socket joint, in which the ball-shaped head of the femur is positioned within the socket-shaped acetabulum of the pelvis. Various degenerative diseases and injuries may require replacement of all or a portion of a hip using synthetic materials, typically metals, ceramics, or plastics.

A standard hip replacement includes two bearing surfaces that form an interface between the femoral head and the acetabulum. The first bearing surface is typically part of a prosthesis shell or acetabular cup, which may be formed of metal, ceramic material. A liner (conventionally formed of a polymer such as ultra high molecular weight polyethylene, a ceramic material, or in some cases, a metal liner) is then fit tightly within the shell to provide an inner bearing surface that receives and cooperates with an artificial femoral head in an articulating relationship to accommodate the relative movement between the femur and the acetabulum.

The cup, or a cup and liner assembly, is typically fixed either by placing screws through apertures in the cup or by securing the cup with cement. In some cases, only a liner is cemented in a patient due to poor bone stock. In other cases, a cup having a porous surface may be press fit into an acetabular surface after the surface is prepared with a reaming tool.

Restoration of a patient's natural anatomy (e.g., restoring the normal center of hip rotation) is accomplished by acetabular preparation. Preoperative templating (e.g., preoperative X-rays including an anteroposterior (AP) view of the pelvis and hips, an AP view of the affected hip and femur, and a lateral view of the affected hip) is often used to properly reconstruct the hip joint.

Using the existing anatomy as the reamer guide, the patient's acetabulum is expanded concentrically using acetabular reamers of increasing diameter (e.g., in 1 mm to 2 mm increments) until a desired acetabular diameter is achieved, for example, when a subchondral bone is reached. Acetabular reaming is directed in approximately 45 degrees of abduction and 20 degrees of anteversion relative to the acetabulum for final position of the acetabular component. Once the patient's acetabulum has been reamed, the appropriate acetabular shell is selected, attached to the acetabular cup positioner/impactor, and inserted into the acetabulum.

With current systems, the acetabular shell is typically aligned to the patient's acetabulum using an external X-bar located above the operating table on which the patient is positioned. The X-bar is positioned so that the vertical bar of the X-bar is perpendicular to the long axis of the patient's body and the appropriate crossbar (e.g., left or right) aligns with the long axis of the patient's body. Vertical orientation of the X-bar and alignment of the appropriate cross bar with the body axis provides 45 degrees of abduction and 20 degrees of anteversion. The inserter is then firmly tapped with a mallet until the acetabular cup is fully seated.

With current systems, the use of a generalized X-bar positioning system is often insufficient to properly align the acetabular implant as a result of anatomical differences between patients or differences in patient position during surgery. Misalignment of the acetabular implant can result in leg length discrepancies, inadvertent lateralization of the hip center of rotation, or both. The surgeon will often have to perform a second or subsequent surgery (e.g., an acetabular revision surgery) to correct the misalignment. This can be time consuming and expensive, and may subject the patient to additional health risks.

SUMMARY

Disclosed herein are systems, devices, and methods for aligning orthopedic implants using a patient-matched alignment tool. In particular, a patient-matched acetabular alignment tool for use in aligning acetabular implants is disclosed. The patient-matched acetabular alignment tool includes a mounting member and one or more leg members attached to respective attachment sites on the mounting member. The leg members are actuatable to a predetermined configuration with respect to the mounting member or tool and, when so actuated, the leg members extend outwardly from the mounting member and thereby align the mounting member with respect to a predetermined implant axis. The mounting member and leg members facilitate the alignment of the longitudinal axis of the patient-matched acetabular alignment tool with respect to the patient's acetabulum at a predetermined, patient-specific implant angle by forming a support base for the patient-matched acetabular alignment tool on one or more of the patient's anatomic landmark sites.

In some embodiments, an orthopedic device includes a mounting member positioned on an orthopedic implantation tool, the mounting member having a plurality of attachment sites. One or more leg members that correspond with one or more anatomic landmark cites couple with the mounting member at one of the plurality of attachment sites. Each leg member is actuatable to a predetermined configuration with respect to the tool such that, when actuated to the predetermined configuration, the leg extends outwardly from the longitudinal axis and aligns the mounting member with a predetermined implant axis.

In certain implementations, two or more leg members coupled with a mounting member have different shapes, different widths, different thicknesses, different material compositions, or a combination thereof. In certain implementations, at least two leg members are used, and the predetermined configuration includes a first leg member having a different length than a second leg member. The anatomic landmark site for a respective leg member may be a bony landmark. Bony landmarks include an anterior inferior iliac spine, acetabular limbus, ischial spine, pubic tubercle, or acetabular notch.

In certain implementations, each leg member has at least one characteristic that is selected based on a model of a patient's anatomy and the desired implant axis. The implant axis defines a desired version angle and a desired inclination angle with respect to a patient's acetabulum. The desired implant axis may be patient-matched and indicate a preselected path over which an implant is to be oriented with respect to a patient's bone.

In certain implementations, the leg members are retractable with respect to the mounting member. The orthopedic device may include an expanding mechanism that causes retracted leg members to expand when actuated.

In some embodiments, a method for aligning an orthopedic tool includes selecting at least one leg member from a plurality of leg members, and each selected leg member corresponds to a respective anatomic landmark site. The method includes coupling each of the selected leg members to a mounting member and aligning the mounting member such that each of the selected leg members mates with its respective anatomic landmark site. In certain implementations, a method includes selecting at least one leg member from a plurality of leg members, wherein each selected leg member has a pre-determined configuration that corresponds to a respective anatomic landmark site. The method includes coupling each selected leg member to a mounting member at a location that corresponds to the predetermined configuration, and actuating the mounting member such that each selected leg member reaches its respective anatomic landmark site.

In certain implementations, the two or more selected leg members have different lengths, different widths, different thicknesses, different material compositions, or a combination thereof.

In certain implementations, the method includes creating a computerized model of a patient site and identifying anatomic landmark sites from the model. A desired implant axis is determined from the patient site model, and at least one leg member is selected based on the implant axis and one of the anatomic landmark sites. Determining the implant axis includes defining a desired version angle and defining a desired inclination angle with respect to a patient's acetabulum. The method further includes extracting data from at least one of an X-ray, CT scan, and an MRI scan and creating a physical model of the patient site based on the computerized model. The mounting member is positioned on the patient model such that each leg member mates with its respective anatomic landmark site on the physical model, and a longitudinal axis of the mounting member positioned on the physical model is compared with a desired implant axis.

In certain implementations, the method includes retracting the leg member with respect to the mounting member and expanding the leg members with respect to the mounting member when the mounting member is inserted into a patient site.

In some embodiments, a kit for an orthopedic implant includes a first leg member having a first configuration, at least one additional leg member having a second configuration different from the first configuration, and a mounting member having attachment sites for coupling with the first leg member and the at least one additional leg member.

In certain implementations, the first configuration and the second configuration include different lengths, different widths, different thicknesses, different material compositions, or a combination thereof. In certain implementations, the leg members are retractable with respect to the mounting member.

In some embodiments, a method for aligning an orthopedic tool includes selecting at least one leg member from a plurality of actuatable leg members, coupling each selected actuatable leg member to a mounting member, inserting the mounting member into a patient site, and aligning the mounting member with respect to the patient site by actuating each of the selected leg members until it mates with a respective anatomic landmark site.

In certain implementations, selecting at least one leg member includes selecting two or more leg members having different lengths, different widths, different thicknesses, different material compositions, or a combination thereof.

In certain implementations, the method includes modeling the patient site and identifying anatomic landmark sites from the model. A desired implant axis is determined from the patient site model, and at least one leg member is selected based on the implant axis and one of the anatomic landmark sites. Determining a desired implant axis includes defining a desired version angle and defining a desired inclination angle with respect to the patient's acetabulum.

In certain implementations, the method includes retracting the leg members with respect to the mounting member and expanding the leg members with respect to the mounting member when the mounting member is inserted into a patient site.

In some embodiments, a method for manufacturing an orthopedic tool includes receiving data associated with at least one of an X-ray, a CT scan, and an MRI scan, determining an implant axis based on the received data, determining a respective configuration for one or more leg members based on the received data, and producing the one or more leg members according to the determined configurations.

In certain implementations, determining a respective configuration includes determining the respective configuration for two or more leg members having different lengths, different widths, different thicknesses, different material compositions, or a combination thereof. The method may include coupling each leg member to a mounting member positioned on the orthopedic implantation tool, and the mounting member may have a plurality of attachment sites for coupling with leg members.

In certain implementations, the method includes creating a computerized model of a patient site based on the received data and identifying anatomic landmark sites from the model. The method includes determining an implant axis from the patient site model. Determining a desired implant axis includes defining a desired version angle and defining a desired inclination angle with respect to the patient's acetabulum. The method includes creating a physical model of the patient site based on the computerized model and positioning the mounting member on the physical model such that each leg member mates with its respective anatomic landmark site on the physical model. A longitudinal axis of the mounting member positioned on the physical model is compared with the determined implant axis.

In certain implementations, the respective configuration includes one of a length, a width, a thickness, a material composition, and a combination thereof. Each leg member is actuatable to a predetermined configuration with respect to the tool such that, when activated to that predetermined configuration, the leg extends outwardly from a longitudinal axis of the tool and aligns the tool with the determined implant axis.

Variations and modifications of these embodiments will occur to those of skill in the art after reviewing this disclosure. The foregoing features and aspects may be implemented, in any combination and subcombinations (including multiple dependent combinations and subcombinations), with one or more other features described herein. The various features described or illustrated above, including any components thereof, may be combined or integrated in other systems. Moreover, certain features may be omitted or not implemented.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which:

FIGS. 4A-B show an illustrative patient-matched acetabular alignment tool having different leg members selected to change the longitudinal axis of the illustrative tool;

DETAILED DESCRIPTION

To provide an overall understanding of the systems, devices, and methods described herein, certain illustrative embodiments will be described. Although the embodiments and features described herein are specifically described for use in connection with acetabular systems, it will be understood that all the components, adjustable systems, manufacturing methods, and other features outlined below may be combined with one another in any suitable manner and may be adapted and applied to medical devices and implants to be used in other surgical procedures, including, but not limited to: knee arthroplasty, shoulder arthroplasty, as well as foot, ankle, hand, and other extremity procedures.

Figure 1:
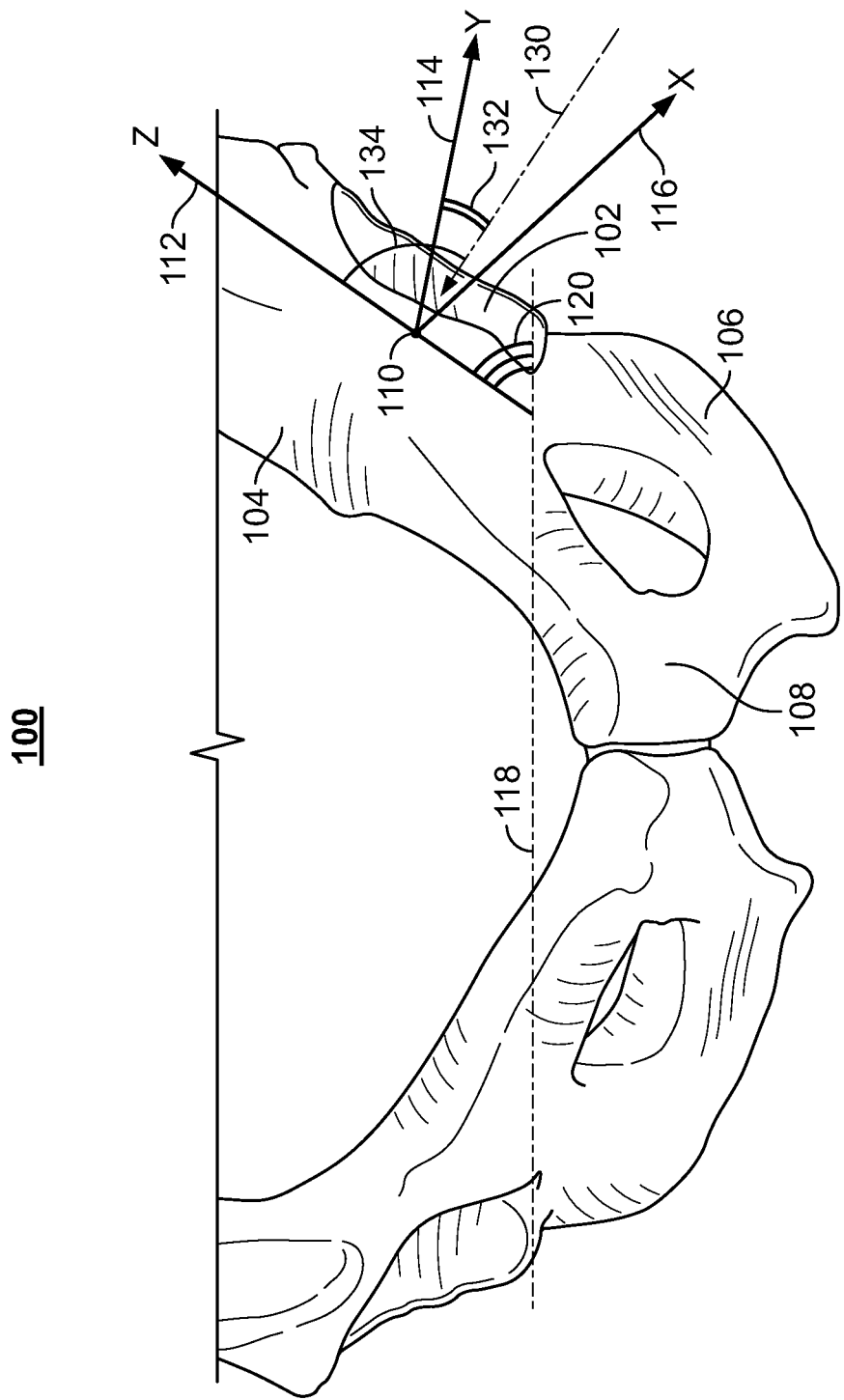
FIG. 1 shows an illustrative pelvic girdle and reference system.

FIG. 1 shows an illustrative pelvic girdle and reference system for use in patient-matched alignment techniques. The patient's pelvic girdle 100 includes acetabulum 102, ilium 104, ischium 106, and pubis 108. A coordinate system, such as a local Cartesian coordinate system, may be used to describe each particular patient's anatomy. For example, the local coordinate system may include origin 110 (e.g., the center of the patient's acetabulum), z-axis 112 (e.g., an axis that extends parallel to the acetabular rim), y-axis 114 (e.g., an axis perpendicular to z-axis 112 in the coronal plane), and x-axis 116 (e.g., an axis orthogonal to y-axis 114 and z-axis 112). Hilgenreiner's line 118 is defined by a horizontal line between the two triradiate cartilage centers of the hips and may be used to determine acetabular angle 120, the angle between Hilgenreiner's line 118 and z-axis 112. As an example, the normal adult range of acetabular angle 120 is approximately between 33 degrees and 38 degrees.

The longitudinal axis of an orthopedic implant tool (e.g., the inserter shaft of a positioner or a patient-matched acetabular alignment tool) is aligned with the patient's anatomy to restore the normal center of hip rotation. A desired longitudinal axis for an orthopedic implant tool is denoted by implant axis 130, which may be a patient-matched implant axis indicative of a pre-selected path over which an implant is to be oriented with respect to a patient's bone. Implant axis 130 forms version angle 132 (the angle between y-axis 114 and implant axis 130) and inclination angle 134 (the angle between z-axis 112 and implant axis 130). For example, implant axis 130 may be aligned such that version angle 132 corresponds to 20 degrees of anteversion and inclination angle 134 corresponds to 20 degrees of anteversion.

Figure 2:
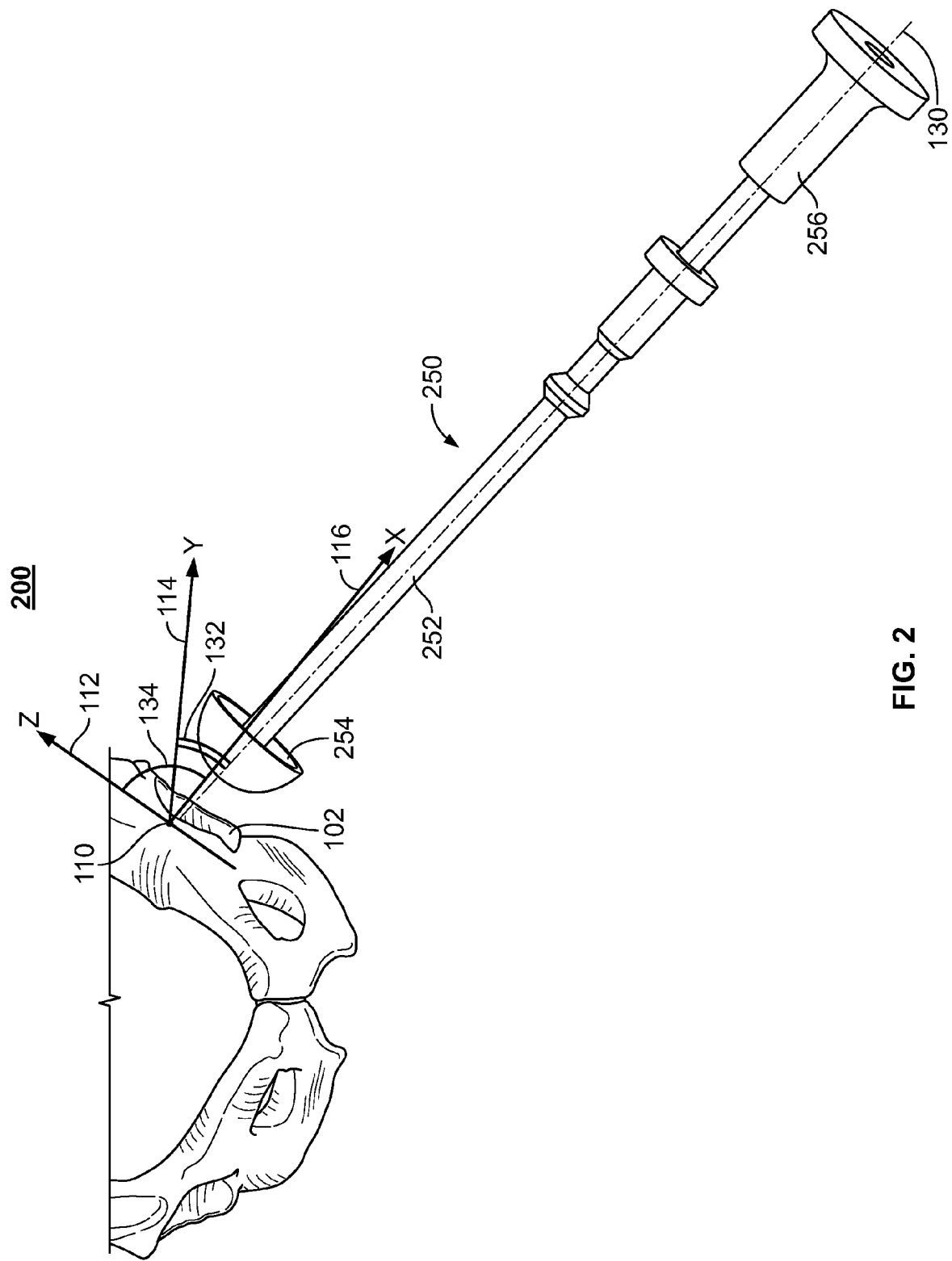
FIG. 2 shows an illustrative acetabular positioner.

FIG. 2 shows a perspective of the illustrative acetabular implant system 200 that includes acetabulum 102 and acetabular positioner/impactor 250. The local coordinate system used to describe the patient's anatomy includes an origin 110, z-axis 112, y-axis 114, and x-axis 116. The longitudinal axis of acetabular positioner/impactor 250 is denoted by implant axis 130, which forms version angle 132 and inclination angle 134.

The acetabular positioner/impactor 250 includes an inserter shaft 252, acetabular cup member 254 (e.g., acetabular shell, cup, cage, or augment), and impactor 256. Once the acetabulum 102 has been reamed, the appropriate configuration (e.g., diameter, shape, material) of the acetabular cup member 254 is selected. The acetabular cup member 254 is attached to acetabular positioner/impactor 250, inserted into acetabulum 102, seated in acetabulum 102 (e.g., by striking impactor 256 with a mallet), and detached from acetabular positioner/impactor 250, which is then removed from the patient's body. Acetabular cup member 254 may be attached to acetabulum 102 in any suitable way, for example with bone cement or mechanically using screws.

Figure 3A:
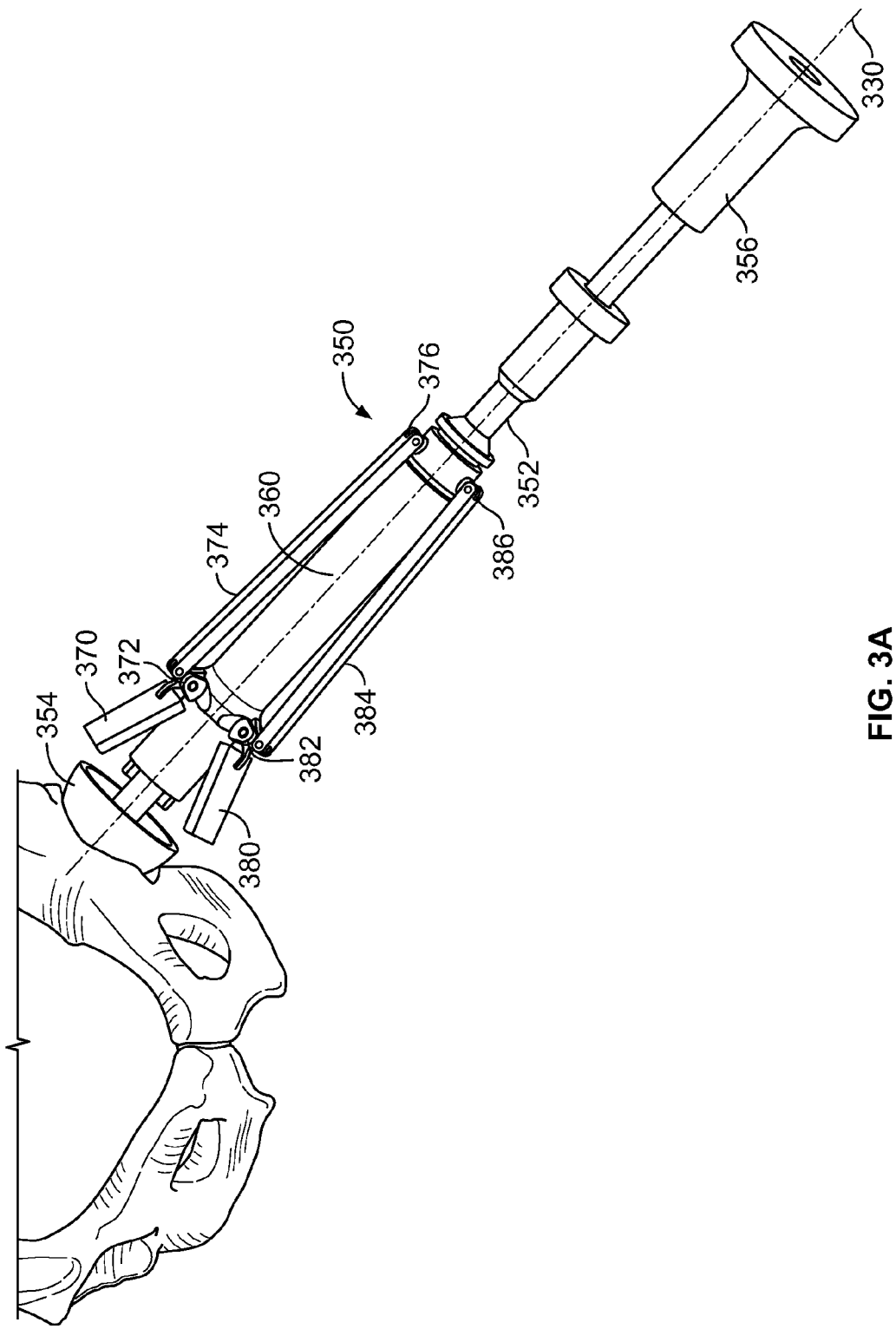
FIGS. 3A-B show an illustrative patient-matched acetabular alignment tool.

FIG. 3A shows a perspective of an illustrative acetabular implant system 300 that includes a patient-matched acetabular alignment tool 350. Patient-matched acetabular alignment tool 350 includes inserter shaft 352, acetabular cup member 354, and impactor 356. In addition, patient-matched acetabular alignment tool 350 includes leg members and a mounting member for improving the alignment of the implant axis with the patient-matched angles of version and inclination. For example, patient-matched acetabular alignment tool 350 includes leg member 370 and leg member 380 which are attached to mounting member 360 at attachment site 372 and attachment site 382, respectively.

Inserter shaft 352, acetabular cup member 354, impactor 356, and a placement head (not shown due to perspective view of FIG. 3A) may be pre-assembled by a manufacturer. For assembly, the placement head is removed from the end of inserter shaft 352, mounting member 360 (with leg members 370 and 380 attached in a retracted position) slides up inserter shaft 352, and the placement head is reattached to the end of inserter shaft 352. Acetabular cup member 354 is then attached to the placement head to form the patient-matched acetabular alignment tool 350.

Leg member 370 and leg member 380 are connected to the mounting member at positions that align the leg members to particular patient acetabular bony landmarks (e.g., acetabular bony landmarks such as an anterior inferior iliac spine, acetabular limbus, ischial spine, pubic tubercle, acetabular notch) to align the mounting member 360 with implant axis 330. The configuration of leg member 370 and leg member 380 is patient-matched by specifically structuring the leg member 370 and leg member 380 with a configuration that, when applied to a particular patient, matches the anatomy of the patient. In particular, the leg member 370 and leg member 380 have pre-selected, patient matched characteristics, such as shape, length, width, thickness, and attachment site location (e.g. 372 and 374) with respect the tool, so that the leg members will be positioned against the patient's bone at specific land marks in the predetermined configuration when the legs are deployed. In certain embodiments, leg member 370 and leg member 380 are labeled with the anatomic bony landmarks with which they should mate. The legs may have end surfaces that mate with specific bone sites.

In one implementation, the leg members are coupled to the mounting member 360 at pre-determined sites along the member 360, the mounting member 360 is actuated, and the legs expand until reaching their respective bony land marks. The legs may have one or more other pre-determined characteristics to correspond to the patient's bone when the legs are actuated. To improve the stability of patient-matched acetabular alignment tool 350 during operation, patient-matched acetabular alignment tool 350 may include a third leg member (e.g., leg member 390 of FIG. 3B) to form a tripod configuration about mounting member 360. By preselecting the configuration of the leg member and their attachment sites according to patient matched information, the alignment tool 350 can be accurately positioned to achieve the proper implant axis.

In certain embodiments, patient-matched acetabular alignment tool 350 includes support member 374 and support member 384 for use in retracting and expanding the leg members 370 and 380, respectively. Leg member 370 is retracted and expanded by actuation of support member 374, which is coupled to the mounting member 360 at attachment site 372 and pivots about the coupling 376. Similarly, leg member 380 is retracted and expanded by actuation of support member 384, which is coupled to the mounting member 360 at attachment site 382 and pivots about the coupling 386. Support members 374 and 384 may be actuated by any suitable actuation mechanism or technique, such as by pulling a lever, pulling a handle, turning a hand crank, pressing a switch, or performing any other suitable feature. The retraction of the leg members collapses them, reducing their profile with respect to the mounting member 360 and thereby decreasing the insertion profile of patient-matched acetabular alignment tool 350. The reduced profile allows for a less invasive surgical insertion of the acetabular cup member. Once inserted in the patient's soft tissue, the expansion of the leg members (e.g., to form a tripod) allows for increased stabilization of patient-matched acetabular alignment tool 350 by increasing the tool's support base and contacting the patient's natural acetabular bony landmarks.

Figure 3B:
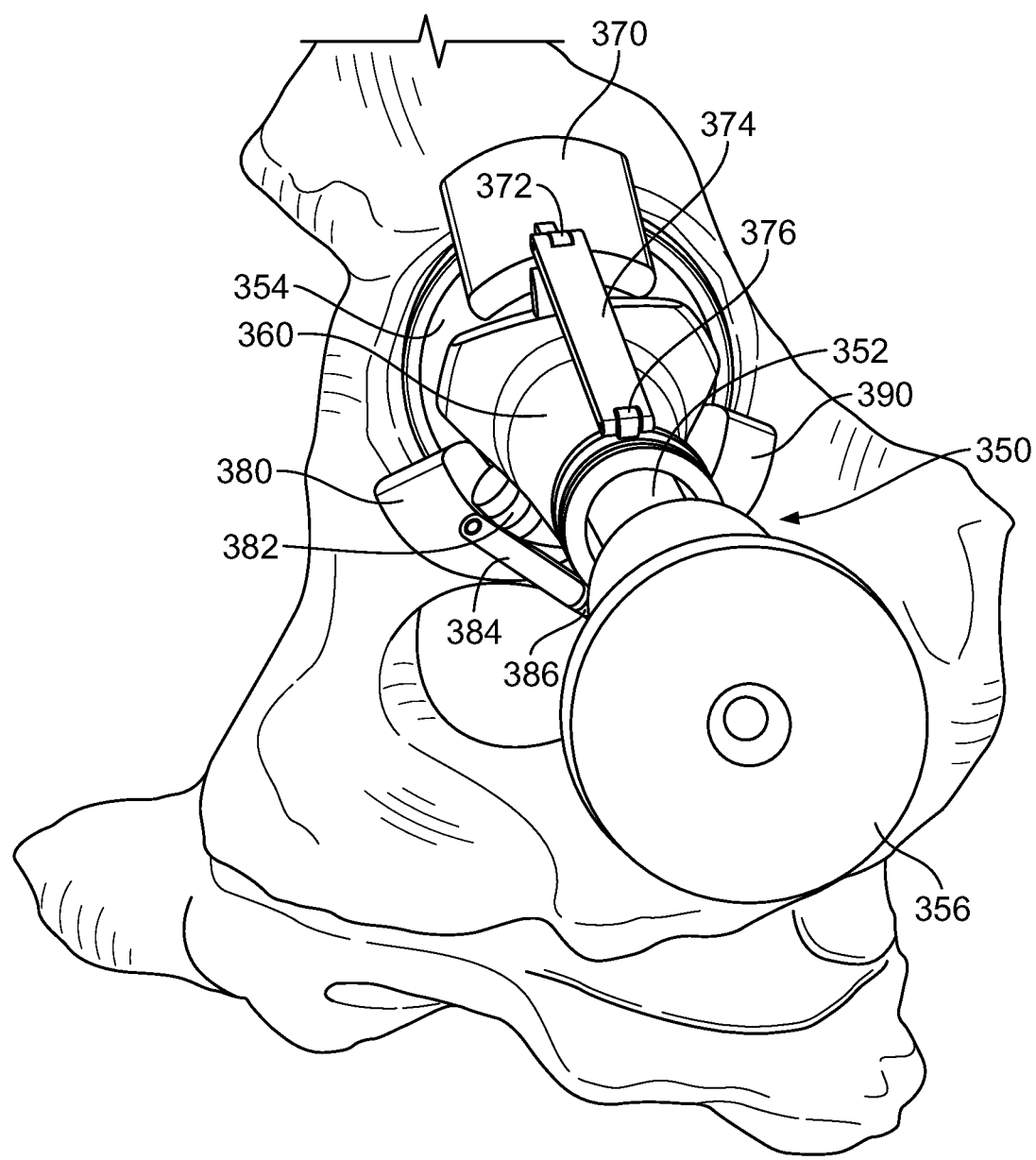

FIG. 3B shows another perspective of illustrative acetabular implant system 300 that includes patient-matched acetabular alignment tool 350. Patient-matched acetabular alignment tool 350 includes leg member 370, leg member 380, and leg member 390, which are arranged to form a tripod configuration about mounting member 360. Leg member 390 is attached to mounting member 360 at an attachment site similar to attachment site 372. In certain embodiments, leg member 390 is retracted and expanded by operation of a support member similar to support member 384, which is coupled to the mounting member 360 at an attachment site similar to attachment site 382 and pivots about a coupling similar to coupling 386. The attachment site, support member, and coupling associated with leg member 390 are not shown due to the perspective view of FIG. 3B.

FIG. 4A shows an illustrative acetabular implant system 400 similar to the implant system 300 described with reference to FIGS. 3A and 3B, with leg member 370, leg member 380, and mounting member 360 configured so that the leg member 370 and leg member 380 align implant axis 330 with the patient's normal center of hip rotation (e.g., by achieving the desired angles of inclination and version). As shown, the leg members are in an actuated position so as to contact the landmark sites 404 and 406 along the acetabular rim of acetabulum 402. These are positions at angles of approximately 40 degrees and 30 degrees, respectively, with respect to the axis 330 so that upon contacting the sites 404 and 406, the legs stabilize the entire device. The stabilizer device has its longitudinal axis aligned in parallel with the implant axis 330. Anatomic landmark sites 404 and 406 may be any suitable location on the patient's anatomy for orienting patient-matched acetabular alignment tool 350, such as one or more natural acetabular bony landmarks (e.g., acetabular bony landmarks such as an anterior inferior iliac spine, acetabular limbus, ischial spine, pubic tubercle, acetabular notch).

Preoperative templating may be used to determine the locations of the anatomic landmark sites and the configurations of the leg members that will be connected thereto to properly reconstruct the hip joint. Preoperative templating may include analysis of data extracted from preoperative X-rays, computed tomography (CT) scans, magnetic resonance imaging (MRI) scans, or any other suitable technique. In certain embodiments, the extracted data corresponds to an anteroposterior (AP) view of the pelvis and hips, an AP view of the affected hip and femur, and a lateral view of the affected hip. In certain embodiments, a computerized model of a patient site is created based on the preoperative data from which the anatomic landmark sites may be identified.

In certain implementations, a surgeon or other medical professional selects leg members 370 and 380 from a kit of leg members based on the anatomic landmark sites to which they will be connected to orient the implant axis 330 of patient-matched acetabular alignment tool 350. In certain implementations, the implant axis 330 and the configuration (e.g., length, width, thickness, material composition) of leg members 370 and 380 necessary to orient mounting member 360 with implant axis 330 is determined by a processor (e.g., a computer processor associated with a manufacturing center) based on the preoperative X-ray, CT, and/or MRI data.

In certain implementations, leg members 370 and 380 may be specifically manufactured for a particular patient. For example, a manufacturer may receive a patient X-ray, CT scan, MRI scan, or any other suitable data and determine implant axis 330 based on the received data. The configuration of leg members 370 and 380 may then be determined to orient mounting member 360 with implant axis 330. Leg members 370 and 380 may then be manufactured according to their configurations and sent to the surgeon who will perform the surgery.

Figure 4B:
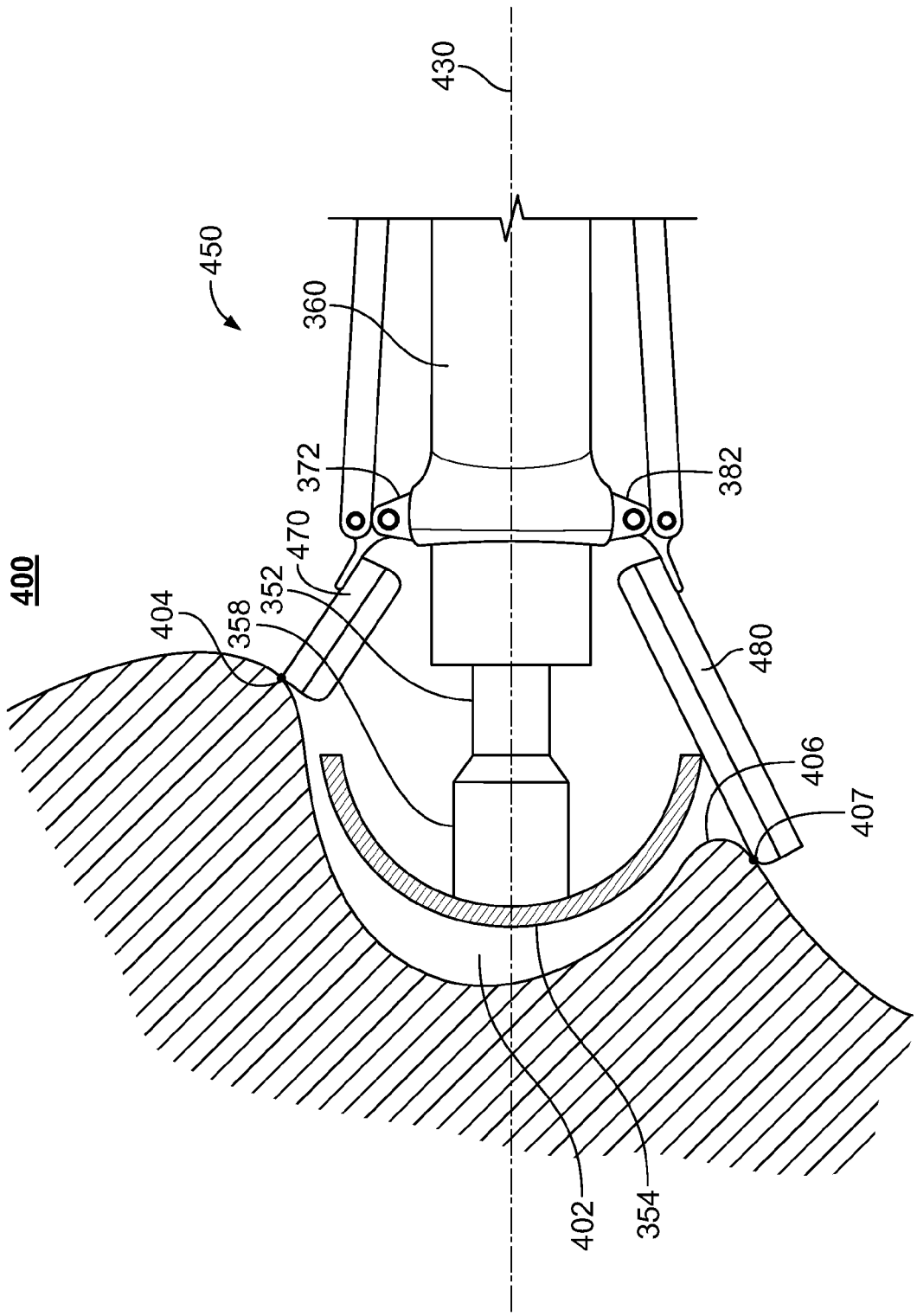

The leg members couple to the mounting member at a predetermined orientation that aligns the tool's longitudinal axis, with the desired implant axis. That is achieved specifically for each patient by providing a specific shape, length, width, thickness or other feature to each leg member, so that it will contact the patient's bone areas at predetermined, specific locations. FIG. 4B shows a two-dimensional view of illustrative acetabular implant system 400 similar to the system 400 shown in FIG. 4A but with different leg members 470 and 480 selected to change the longitudinal axis of the illustrative tool (e.g., to change implant axis 330 of FIG. 4A to implant axis 430 of FIG. 4B).

Leg member 470 and leg member 480 are selected to align the longitudinal axis 430 with the patient's normal center of hip rotation by contacting anatomic landmark site 404 and anatomic landmark site 407 (which is different location or feature than anatomic landmark site 406), respectively. As shown, leg member 470 is shorter than the leg member 370 in FIG. 4A to achieve implant axis 330. Alternatively, leg member 480 is longer than leg member 380 in FIG. 4A to achieve a different implant axis and to contact anatomic landmark site 407 (which is located further from the center of acetabulum 402 than anatomic landmark site 406).

Figure 5:
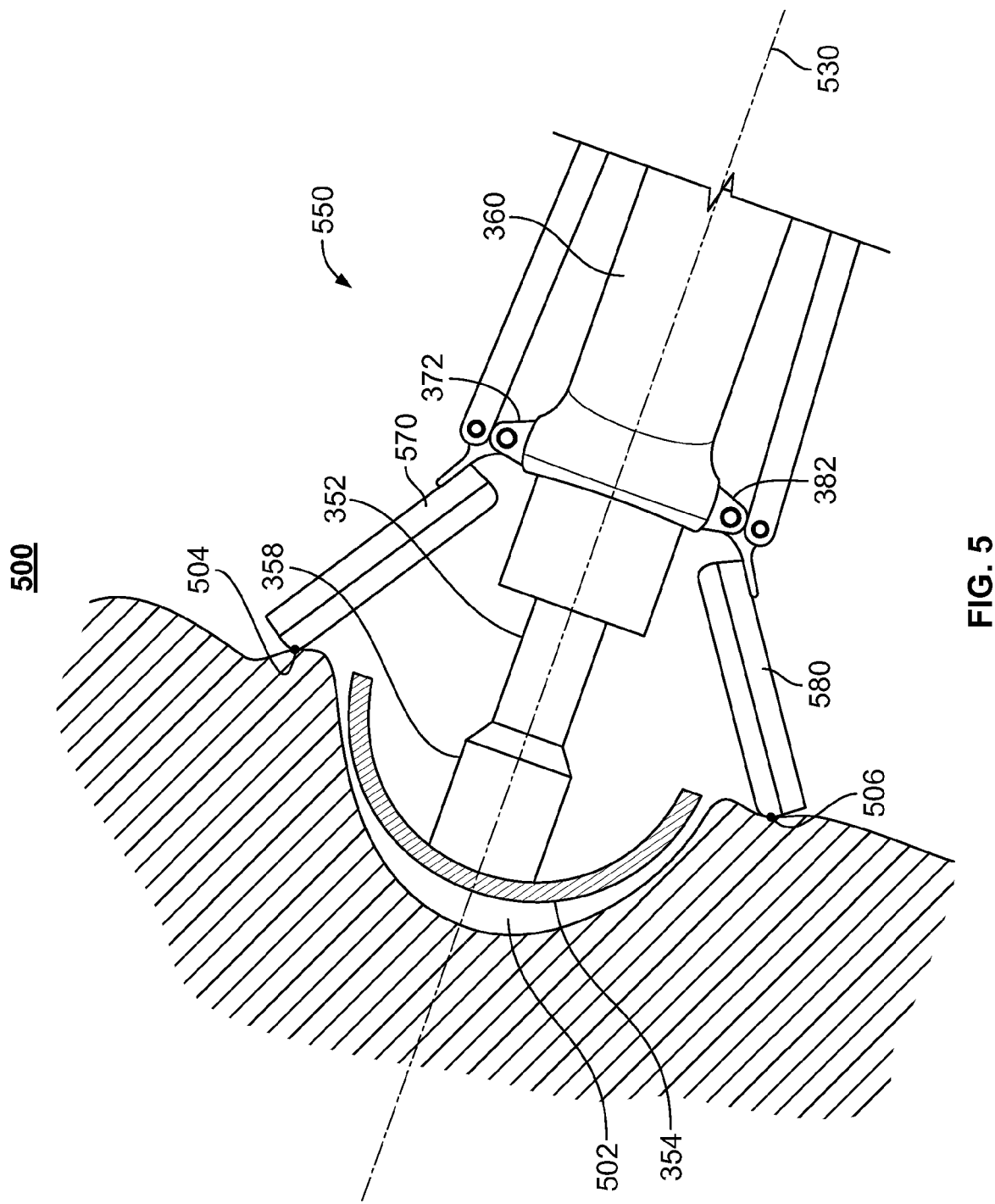
FIG. 5 shows an illustrative patient-matched acetabular alignment tool having different leg members selected to accommodate different anatomical landmark sites.

FIG. 5 shows a two-dimensional view of illustrative acetabular implant system 500 that includes patient-matched acetabular alignment tool 550 having different leg members selected to accommodate different anatomical landmark sites than those shown in FIG. 4. For example, the acetabulum 502 may be associated with a different patient or a different side of the patient than acetabulum 402 of FIG. 4.

Patient-matched acetabular alignment tool 550 includes inserter shaft 352, acetabular cup member 354, and placement head 358. Leg member 570 (having a different configuration than leg member 370 of FIG. 4A) and leg member 580 (having a different configuration than leg member 380 of FIG. 4A), which are attached to mounting member 360 at attachment site 372 and attachment site 382, respectively. Leg member 570 and leg member 580 are selected to align implant axis 530 with the patient's normal center of hip rotation by contacting anatomic landmark site 504 and anatomic landmark site 506, respectively. In an example, leg member 570 is shorter and thinner than leg member 580 to achieve implant axis 530.

Figure 6A:
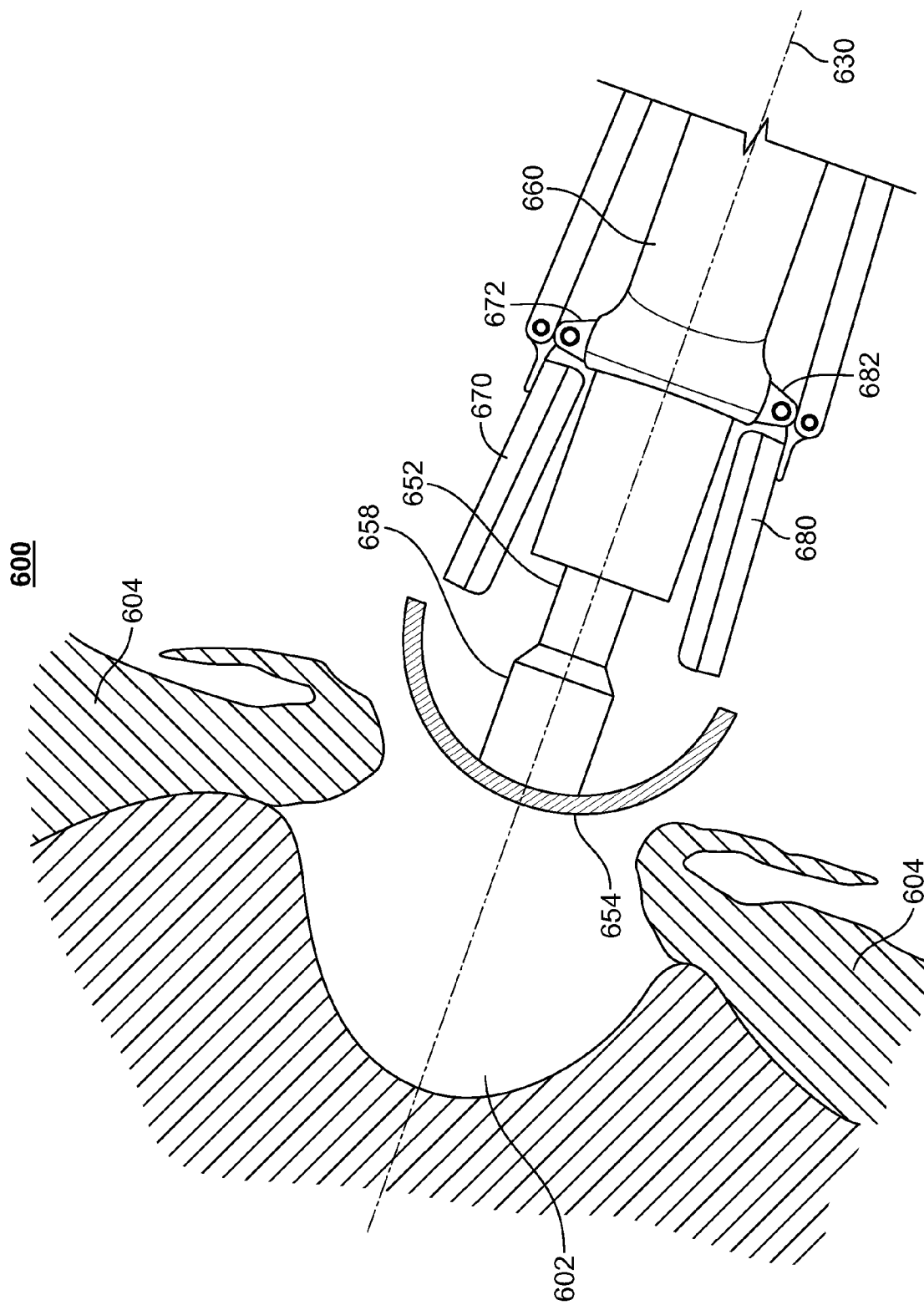
FIG. 6A shows the insertion of an illustrative patient-matched acetabular alignment tool having retracted leg members.
Figure 6B:
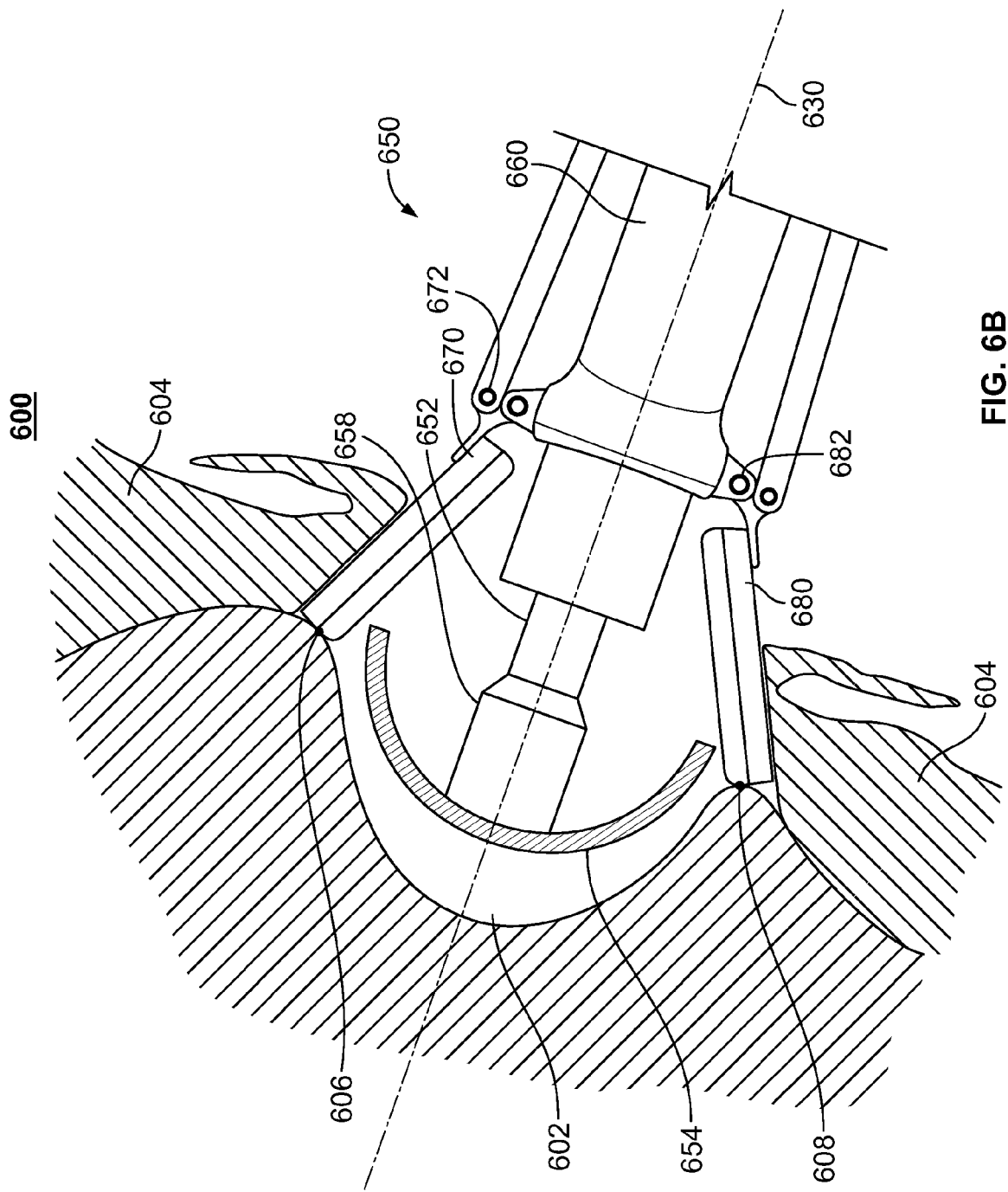
FIG. 6B shows the alignment of the illustrative patient-matched acetabular alignment tool of FIG. 6A by expanding the retracted leg members.
Figure 6C:
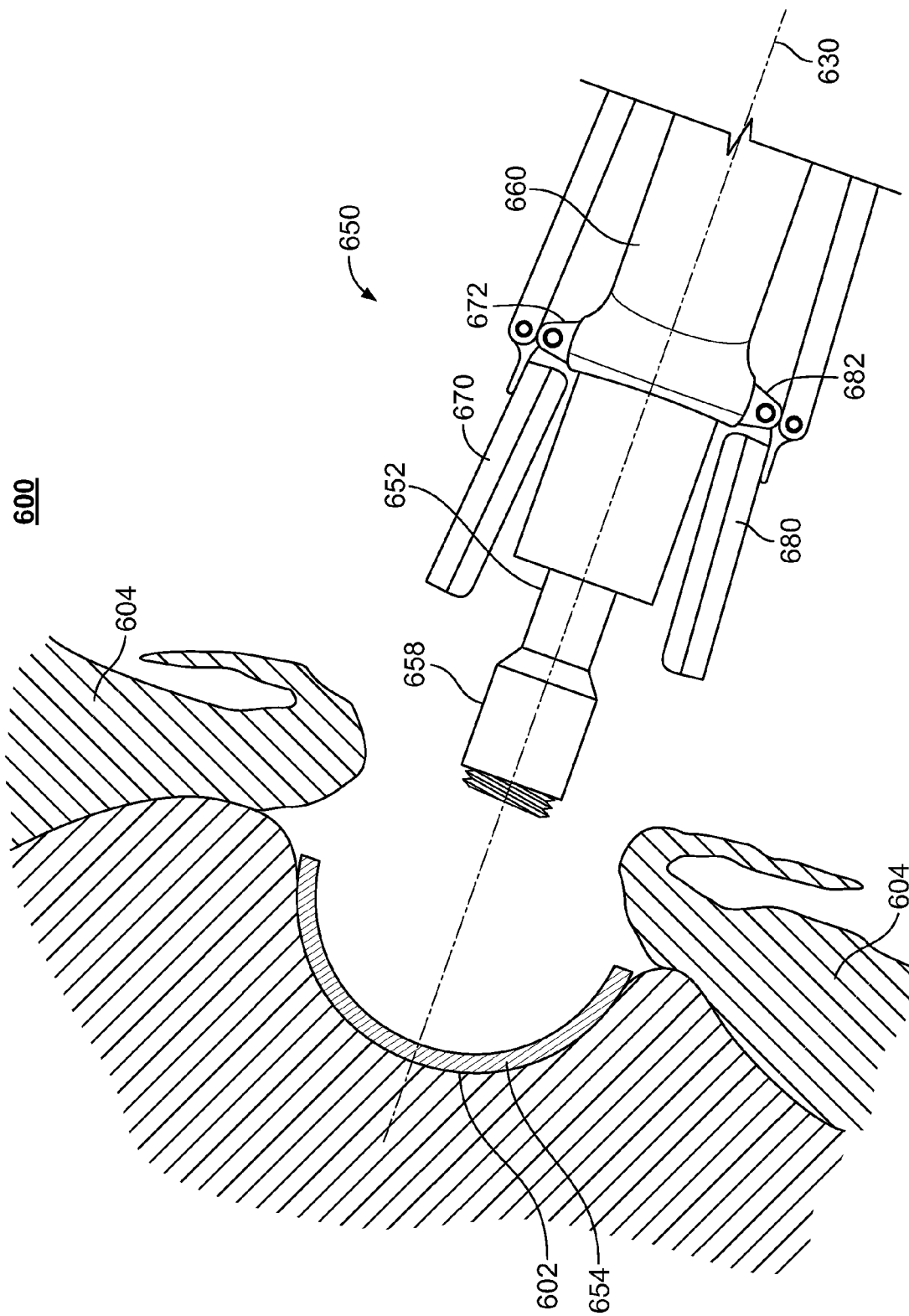
FIG. 6C shows the removal of the illustrative patient-matched acetabular alignment tool of FIG. 6B by detaching the acetabular cup member and retracting the expanded leg members.

Illustrations of the operation of an illustrative patient-matched acetabular alignment tool having retractable/expandable leg members are shown in FIGS. 6A-C. The retraction of the leg members collapses them, reducing their profile with respect to the mounting member and thereby decreasing the insertion profile of the patient-matched acetabular alignment tool. The reduced profile allows for a less invasive surgical insertion of the acetabular cup member. Once inserted in the patient's soft tissue, the expansion of the leg members (e.g., to form a tripod) allows for increased stabilization of the patient-matched acetabular alignment tool by increasing the tool's support base and contacting the patient's natural acetabular bony landmarks.

FIG. 6A shows a two-dimensional view of illustrative acetabular implant system 600 that includes patient-matched acetabular alignment tool 650 having retracted leg members for insertion into the patient's soft tissue 604. Patient-matched acetabular alignment tool 650 includes inserter shaft 652, acetabular cup member 654, and placement head 658. Acetabular cup member 654 is temporarily attached to placement head 658 (e.g., by friction or threading) so that acetabular cup member 654 may be detached from placement head 658 once seated in acetabulum 602. In addition, patient-matched acetabular alignment tool 650 includes leg member 670, leg member 680, and mounting member 660. Leg members 670 and 680 are attached to mounting member 660 at attachment site 672 and attachment site 682, respectively.

In certain embodiments, leg member 670 and leg member 680 are retracted by actuation of support members respectively coupled to each leg member and to mounting member 660 (not shown). The retraction of the leg members allows for a less invasive surgical insertion of the acetabular cup member by decreasing the opening diameter in soft tissue 604 necessary to accommodate the insertion profile of patient-matched acetabular alignment tool 650. The retracted system 600 shown in FIG. 6A is inserted into the patient's soft tissues until the cup 654 seats within the acetabulum.

When the cup 654 reaches the acetabulum, the operator actuates the insertion tool to expand the leg members 670 and 680 into place against the acetabular rim to align the axis 630 of the tool with the desired implant axis. FIG. 6B schematically shows the alignment of the patient-matched acetabular alignment tool 650 of FIG. 6A by expanding the retracted leg members. As shown, the patient-matched acetabular alignment tool 650 having expanded leg member contact the patient's anatomic landmark sites 606 and 608.

In certain embodiments, leg member 670 and leg member 680 are expanded by the actuation of support members respectively coupled to each leg member and to mounting member 660 (not shown). Once inserted in the patient's soft tissue, the expansion of the leg members allows for increased stabilization of patient-matched acetabular alignment tool 650 by increasing the tool's support base and contacting the patient's natural acetabular bony landmarks (e.g., anatomic landmark sites 606 and 608).

FIG. 6C schematically shows the removal of the illustrative patient-matched acetabular alignment tool 650 of FIG. 6B by detaching the acetabular cup member and retracting the expanded leg members. To retract the tool, the operator detaches the tool 650 from the acetabular leg, for example, by unscrewing placement head 658 from cup member 654, and then actuates the leg members by pulling a lever that collapses the leg members. The entire tool 650 is then removed from the patient site.

The foregoing is merely illustrative of the principles of the disclosure, and the systems, devices, and methods can be practiced by other than the described embodiments, which are presented for purposes of illustration and not of limitation. It is to be understood that the systems, devices, and methods disclosed herein, while shown for use in acetabular systems, may be applied to medical devices to be used in other surgical procedures including, but not limited to, knee arthroplasty, shoulder arthroplasty, as well as foot, ankle, hand, and extremities procedures.

Variations and modifications will occur to those of skill in the art after reviewing this disclosure. The disclosed features may be implemented, in any combination and subcombinations (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

What is claimed is:

1. An orthopedic device comprising:
    a mounting member positioned on an orthopedic implantation tool, the mounting member having a plurality of attachment sites;
    one or more leg members that correspond with one or more anatomic landmark sites, wherein each leg member couples with the mounting member at one of the plurality of attachment sites and is actuatable to a predetermined configuration with respect to the tool, such that, when actuated to that predetermined configuration, each leg member extends outwardly from the longitudinal axis and aligns the mounting member with a predetermined implant axis, wherein the leg members are retractable with respect to the mounting member; and
    an expanding mechanism that causes retracted ones of the leg members to expand when actuated.

2. The orthopedic device of claim 1, further comprising two or more leg members having different shapes, different lengths, different widths, different thicknesses, different material compositions, or a combination thereof.

3. The orthopedic device of claim 1, wherein each leg member has at least one feature that is selected based on a model of a patient's anatomy and the desired implant axis.

4. The orthopedic device of claim 1, wherein the implant axis defines a desired version angle with respect to a patient's acetabulum.

5. The orthopedic device of claim 1, wherein the implant axis defines a desired inclination angle with respect to a patient's acetabulum.

6. The orthopedic device of claim 1, wherein the anatomic landmark site comprises at least one bony landmark.

7. The orthopedic device of claim 6, wherein the at least one bony landmark comprises an anterior inferior iliac spine, acetabular limbus, ischial spine, pubic tubercle, or acetabular notch.

8. The orthopedic device of claim 1, wherein the implant axis is a patient-matched implant axis indicative of a pre-selected path over which an implant is to be oriented with respect to a patient's bone.

9. The orthopedic device of claim 1, wherein the predetermined configuration includes a first leg member having a different length than a second leg member.

10. The orthopedic device of claim 1, wherein the expanding mechanism includes a collar and a plurality of support members, wherein each of the support members has a first end connected to the collar and a second end, wherein each leg member is connected to a corresponding one of the attachment sites by a first pivot joint, and wherein each leg member is coupled to the second end of a corresponding one of the support members by a second pivot joint.

11. A method for aligning an orthopedic tool, comprising:
selecting at least one leg member from a plurality of leg members, wherein each selected leg member has a pre-determined configuration that corresponds to a respective anatomic landmark site;
coupling each selected leg member to a mounting member at a location that corresponds to the pre-determined configuration; and
actuating an expanding mechanism of the mounting member such that each selected leg member moves from a retracted position to an expanded position, wherein each of the selected leg members engages its respective anatomic landmark site when in the expanded position.

12. The method of claim 11, wherein selecting the at least one leg member comprises selecting two or more leg members having different lengths, different widths, different thicknesses, different material compositions, or a combination thereof.

13. The method of claim 11, further comprising creating a computerized model of a patient site and identifying anatomic landmark sites from the model.

14. The method of claim 13, further comprising determining a desired implant axis from the patient site model, wherein at least one leg member is selected based on the implant axis and one of the anatomic landmark sites.

15. The method of claim 14, wherein determining a desired implant axis comprises defining a desired version angle with respect to the patient's acetabulum.

16. The method of claim 14, wherein determining a desired implant axis comprises defining a desired inclination angle with respect to the patient's acetabulum.

17. The method of claim 13, further comprising extracting data from at least one of an X-ray, a CT scan, and an MRI scan.

18. The method of claim 17, further comprising creating a physical model of the patient site based on the computerized model.

19. The method of claim 18, further comprising positioning the mounting member on the physical model such that each leg member mates with its respective anatomic landmark site on the physical model.

20. The method of claim 19, further comprising comparing a longitudinal axis of the mounting member positioned on the physical model with a desired axis.

21. The method of claim 11, further comprising retracting the leg members with respect to the mounting member.

22. The method of claim 11, further comprising inserting the mounting member into a patient site prior to the actuating, wherein the mounting member is inserted into the patient site with each of the selected leg members in the retracted position, and wherein the actuating causes the leg members to expand with respect to the mounting member when the mounting member is inserted into the patient site.

23. A kit for an orthopedic implant comprising:
a first leg member having a first configuration;
at least one additional leg member having a second configuration different from the first configuration; and
a mounting member having attachment sites for coupling with the first leg member and the at least one additional leg member, the mounting member further comprising an expanding mechanism;
wherein each of the first leg member and the at least one additional leg member includes a first pivot point configured for connection to the attachment sites and a second pivot point configured for connection to the expanding mechanism.

24. The kit of claim 23, wherein the first configuration and the second configuration comprise different lengths, different widths, different thicknesses, different material compositions, or a combination thereof.

25. The kit of claim 24, wherein the leg members are retractable with respect to the mounting member.

26. The kit of claim 23, wherein the expanding mechanism includes a collar and a plurality of support members, and wherein each support member has a first end connected to the collar and a second end configured for connection to the second pivot point.

27. A method for aligning an orthopedic tool, comprising:
selecting at least one actuatable leg member from a plurality of leg members;
coupling each selected actuatable leg member to a mounting member;
inserting the mounting member into a patient site; and
aligning the mounting member with respect to the patient site by actuating each of the selected leg members until it mates with a respective anatomic landmark site; and
wherein the actuating includes operating an expanding mechanism to move each of the selected leg members from a retracted position to an expanded position, and wherein each of the selected leg members mates with the respective anatomic landmark when in the expanded position.

28. The method of claim 27, wherein selecting the at least one leg member comprises selecting two or more leg members having different lengths, different widths, different thicknesses, different material compositions, or a combination thereof.

29. The method of claim 27, further comprising modeling the patient site and identifying anatomic landmark sites from the model.

30. The method of claim 29, further comprising determining a desired implant axis from the patient site model, wherein at least one leg member is selected based on the implant axis and one of the anatomic landmark sites.

31. The method of claim 30, wherein determining the desired implant axis comprises defining a desired angle with respect to the patient's acetabulum.

32. The method of claim 30, wherein determining a desired implant axis comprises defining a desired inclination angle with respect to the patient's acetabulum.

33. The method of claim 27, further comprising retracting the leg members with respect to the mounting member.

34. The method of claim 33, wherein each of the selected leg members is in the retracted position during the inserting, and wherein the actuating is performed when the mounting member is inserted into the patient site.

35. A method for manufacturing an orthopedic tool, comprising:
   receiving data associated with at least one of an X-ray, a CT scan, and an MRI scan;
   determining an implant axis based on the received data;
   determining a respective configuration for one or more leg members based on the received data; and
   producing the one or more leg member according to the determined configurations;
   coupling each of the leg members to a mounting member positioned on the orthopedic implantation tool, the mounting member having a plurality of attachment sites, wherein each leg member couples to the mounting member at one of the plurality of attachment sites;
   attaching each of the leg members to an expanding mechanism of the orthopedic implantation tool; and
   actuating the expanding mechanism to move each of the leg members from a retracted position to an expanded position; and
   wherein each of the one or more leg members is configured to mate with a corresponding anatomical landmark indicated by the data when in the expanded position.

36. The method of claim 35, wherein the determining the respective configuration for one or more leg members comprises determining the respective configuration for two or more leg members having different lengths, different widths, different thicknesses, different material compositions, or a combination thereof.

37. The method of claim 35, further comprising creating a computerized model of a patient site based on the received data and identifying anatomic landmark sites from the model.

38. The method of claim 37, further comprising determining an implant axis from the patient site model.

39. The method of claim 38, wherein determining a desired implant axis comprises defining a desired version angle with respect to the patient's acetabulum.

40. The method of claim 38, wherein determining a desired implant axis comprises defining a desired inclination angle with respect to the patient's acetabulum.

41. The method of claim 38, further comprising creating a physical model of the patient site based on the computerized model.

42. The method of claim 41, further comprising positioning the mounting member on the physical model such that each leg member mates with its respective anatomic landmark site on the physical model.

43. The method of claim 42, further comprising comparing a longitudinal axis of the mounting member positioned on the physical model with the determined implant axis.

44. The method of claim 35, wherein the respective configuration includes one of a length, a width, a thickness, a material composition, and a combination thereof.

45. The method of claim 35, wherein each leg member extends outwardly from a longitudinal axis of the tool and aligns the tool with the determined implant axis when in the expanded position.

* * * * *